United States Patent [19]

Lanier

[11] Patent Number: 4,495,935
[45] Date of Patent: Jan. 29, 1985

[54] FOOT WARMER

[76] Inventor: Jack K. Lanier, P.O. Box 6397, Jacksonville, Fla. 32205

[21] Appl. No.: 526,449

[22] Filed: Aug. 25, 1983

[51] Int. Cl.³ ............................................. A61F 7/00
[52] U.S. Cl. ................................... 126/204; 237/1 R; 219/211
[58] Field of Search ............. 126/204, 205, 206, 208, 126/209, 210; 237/1 R, 12.3 R; 34/202; 219/211, 201

[56] References Cited

U.S. PATENT DOCUMENTS 2,851,573  9/1958  Muccilli ............................ 126/204
4,241,721 12/1980  Holly ................................. 126/204

FOREIGN PATENT DOCUMENTS 0118551  9/1980  Japan ................................. 126/204

Primary Examiner—Henry Bennett
Attorney, Agent, or Firm—Shlesinger, Arkwright, Garvey & Fado

[57] ABSTRACT

A boot and foot warming device for skiers and other outdoor sportsmen comprising:

a chamber bounded by a top wall having a front and a rear portion, a bottom wall, a back wall and side walls; a leg receiving opening within the front portion of the top wall; a chair structure having a back support mounted upon the top wall rearwardly of the leg receiving opening; a pivoting door hinged to the side walls thereby providing a front wall for the chamber; an air circulating heater mounted within the chamber; the bottom wall being sloped for allowing water run-off; and a drain located in the sloped bottom wall.

10 Claims, 3 Drawing Figures

U.S. Patent  Jan. 29, 1985  4,495,935
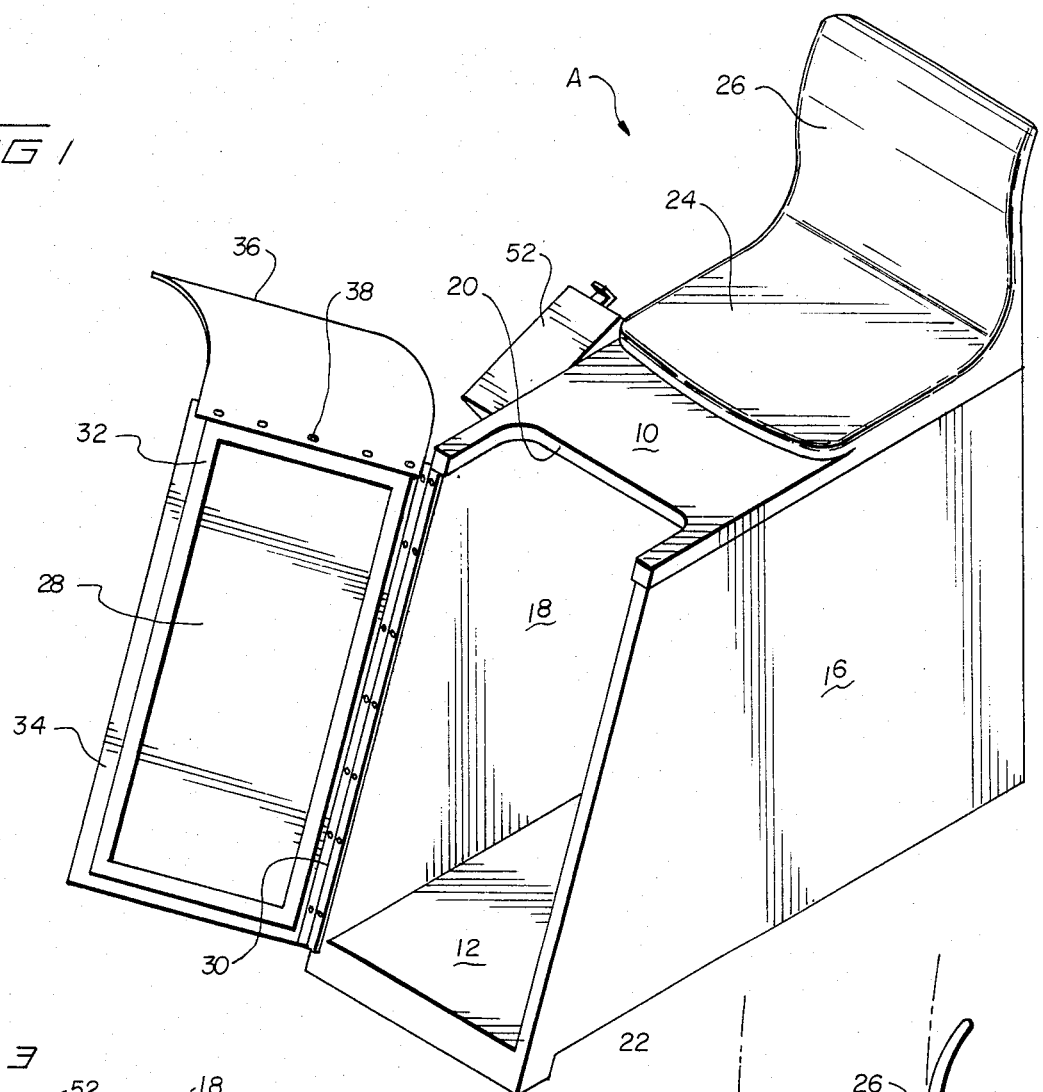
FIG 1
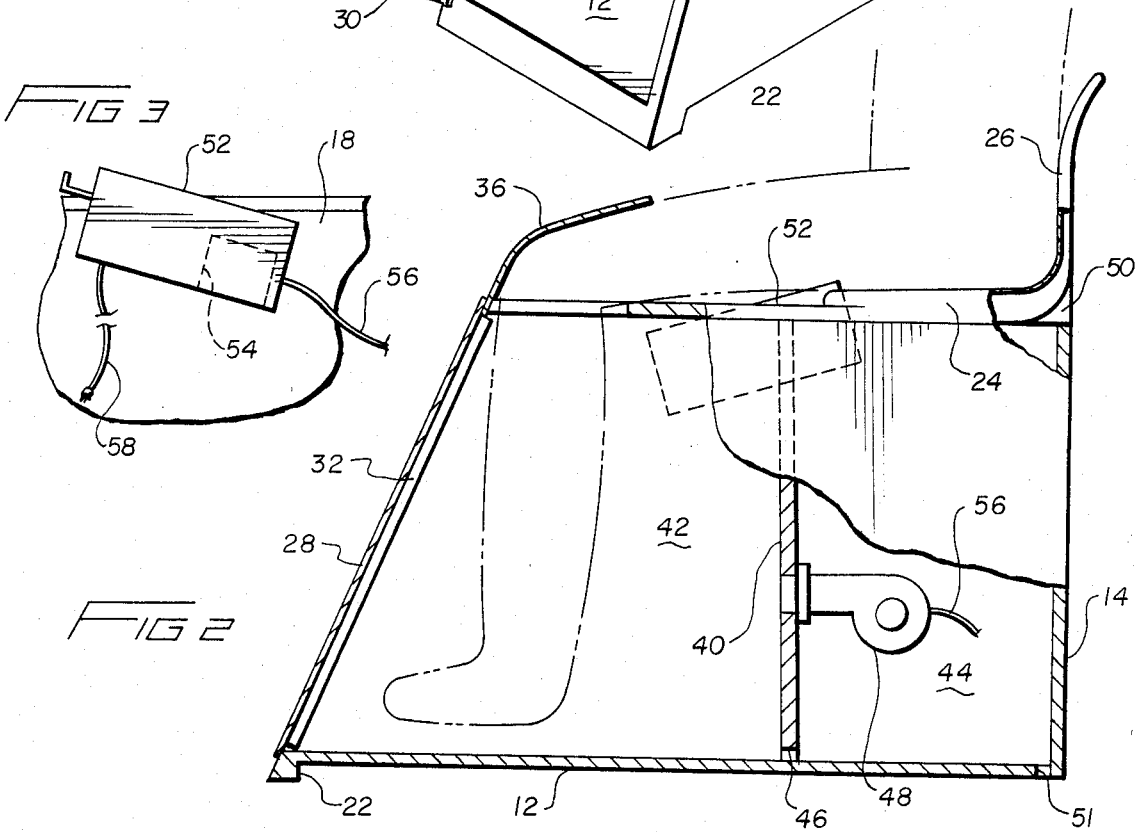
FIG 3
FIG 2

FOOT WARMER

BACKGROUND OF THE INVENTION

This invention relates to a device for warming the boots and feet of skiers or other outdoor sportsmen, and more particularly to a coin operated feet warming device wherein the user is comfortably seated upon the top of the warming device with his lower legs extending into the heating chamber.

In recent years, outdoor sports such as skiing have been gaining in popularity. Those who engage in these activities are often exposed to the elements for extended periods of time. Such exposure can lead to discomfort or more seriously to frost bite particularly in the extremities. It is therefore vital that the sportsman seek refuge from the elements in order to prevent the occurrence of exposure and frost bite.

SUMMARY AND OBJECTS OF THE INVENTION

The present invention provides a simple, yet effective means for allowing those engaged in outdoor sports to regain comfort and proper blood circulation in their feet and hands without the need for seeking shelter within a dwelling.

The foregoing is accomplished by a boot and foot warming device comprising a generally rectangular shaped chamber bounded by top, bottom, back and side walls. A swinging door is hinged at the front portion of the device. A leg receiving opening is cut into the forward most portion of the top wall. A chair structure having a back rest is mounted upon the top wall rearward of the leg opening. The bottom wall is sloped from front to back and a drain is provided in order to allow water run-off. A heater is mounted within the chamber. A flexible flap is attached to the upper portion of the swinging door.

In operation, the user is seated in the chair structure with his thighs supported upon the top wall and his lower legs and feet entering into the chamber through the leg receiving opening. The swinging door is closed, thus sealing the front portion of the chamber. The flexible flap is pulled across the knees and lower thigh portion of the user further sealing the internal chamber. Next, the heater is actuated thereby providing a flow of warm air onto the user's boots and feet. The user may warm his hands by placing them beneath the flexible flap. As snow and ice is melted from the boots, the water is directed toward the rear portion of the chamber by means of the sloped bottom wall, and is subsequently discharged through the drain.

While not being essential to the operation of the device, a coin box may be attached to the device for actuating the heater for a predetermined interval.

It is therefore an object of the present invention to provide a device for warming the feet and boots of an outdoor sportsman.

It is another object of the present invention to provide a boot warming device which is portable and of light weight construction.

A further object of the present invention is to provide a boot warmer which is inexpensive to manufacture and simplistic in design.

A further object of the present invention is to provide a boot warming device which is coin actuated.

Still a further object of the present invention is to provide a boot warmer including means for warming the user's hands.

The foregoing and other objects and advantages of this invention will appear from the following detailed description, taken in conjunction with the accompanying drawings, in which:

FIG. 1 is a perspective view of the boot and feet warming device, with the door in its open position.

FIG. 2 is a left side elevational view of the apparatus in FIG. 1 with portions broken away to show interior portions thereof, FIG. 3 is a fragmentary right side elevational view of the coin box of FIG. 1 with portions shown in phantom lines.

DETAILED DESCRIPTION OF THE DRAWINGS

Referring now to FIGS. 1 and 2, foot and boot warming device A comprised top wall 10, bottom wall 12, back wall 14, and side walls 16 and 18. Slotted leg receiving opening 20 is formed in the front portion of top wall 10. Bottom wall 12 is elevated at its frontal portion by means of leg 22.

A chair structure 24 including a back support 26 is mounted on top wall 10 rearwardly of leg receiving opening 20.

A swinging door 28 is connected to the front portion of side wall 18 by means of hinge 30. Door 28 includes raised sealing strip 32 as well as outwardly extending flanged portion 34. A flexible flap 36 is connected to the upper portion of door 28 by means of fasteners 38. The door 28 is sloped forwardly toward the bottom, because of the slope of the edges of the side walls 16 to permit room for the feet to rest comfortably.

A dividing wall 40 extends transversely across the interior chamber of feet warming device A thereby forming two separated compartments, namely, front chamber 42 and rear chamber 44. Dividing wall 40 includes slotted portion 46 at the bottom thereof.

A heater/blower 48 is mounted in dividing wall 40 for directing heated air into front chamber 42.

An outside air duct or inlet 50 is present in top wall 10 beneath the rear portion of chair 24. A drain 51 is located at the rear most portion of sloped bottom wall 12.

Referring now to FIG. 3, a coin box 52 is mounted on the exterior surface of side wall 18. Coin box 52 is of conventional design, and includes a time controller/actuator 54 (shown in dotted lines). Actuator 54 is connected to heater/blower 48 by means of cord 56. An electrical outlet cord 58 is also connected to coin box 52.

OPERATION

In operation, the user (phantom lines in FIG. 2) is seated in chair 24 with his thighs supported upon top wall 10. The lower legs extend through leg receiving opening 20 and are positioned within front chamber 42. Next, door 28 is closed and flap 36 is extended over the user's knees and upper legs. A coin is inserted into coin box 52, thereby actuating heater 48. Heated air is forced into front chamber 42, while outside air is drawn into rear chamber 44 through airs inlet 50. As ice and snow melt from the boots of the user, water run-off is channeled by means of sloped bottom wall 12 through slot 46 of dividing wall 40 and exits through drain opening 51.

During operation of heater 48, the user may wish to warm his hands by placing them beneath flap 36.

While FIG. 2 shows drain 51 as being mounted in bottom wall 12, it is contemplated that drain 51 may alternatively be located at the lower portion of rear wall 14.

While this invention has been described in connection with different embodiments thereof, it will be understood that it is capable of further modifications, and this application is intended to cover any variations, uses, or adaptations of the invention following, in general, the principles of the invention and including such departures from the present disclosure as come within known or customary practice in the art to which the invention pertains, and as may be applied to the essential features herein before set forth and followed in the scope of the invention for the limits of the appended claims.

What I claim is:

1. A boot and foot warming device for skiers and other outdoor sportsman comprising:
   (a) a chamber bounded by a top wall having a front and a rear portion, a bottom wall, a back wall and side walls;
   (b) a leg receiving opening in said front portion of said top wall;
   (c) said top wall including a seat positioned rearwardly of said leg receiving opening;
   (d) a swinging door hinged to said side wall and providing a front wall for said chamber;
   (e) an air circulating heater mounted within said chamber;
   (f) said bottom wall being sloped for allowing water run-off;
   (g) a drain in said sloped bottom wall;
   (h) a dividing wall extending transversely through said chamber and engaging said top wall, said bottom wall and said side walls; and
   (i) said dividing wall partitioning said chamber into a front chamber and a rear chamber.

2. A boot and foot warmer as in claim 1 and wherein:
   (a) said heater being mounted in said dividing wall and positioned so as to direct heated air into said front chamber.

3. A boot and foot warming device as in claim 1 and wherein:
   (a) said dividing wall having a top and a bottom; and,
   (b) said bottom of said dividing wall being slotted to allow water run-off from said front chamber to said rear chamber.

4. A boot and foot warmer as in claim 1 and wherein:
   (a) an outside air duct opening into said rear chamber.

5. A boot and foot warmer as in claim 2 and wherein:
   (a) said front chamber includes a forward space for positioning the feet under a portion of said door.

6. A boot and foot warming device for skiers and other outdoor sportsmen comprising:
   (a) a chamber bounded by a top wall having a front and a rear portion, a bottom wall, a back wall and side walls;
   (b) a leg receiving opening in said front portion of said top wall;
   (c) said top wall including a seat positioned rearwardly of said leg receiving opening;
   (d) a swinging door hinged to said side wall and providing a front wall for said chamber and forming a movable closure for said leg opening;
   (e) an air circulating heater mounted within said chamber;
   (f) said bottom wall being sloped for allowing water run-off; and
   (g) a drain in said sloped bottom wall.

7. A boot and foot warmer as in claim 6 and wherein:
   (a) a coin box being mounted on said device and connected to said heater for actuating said heater for a predetermined interval.

8. A boot and foot warmer as in claim 6 and wherein:
   (a) said swinging door including a top and a bottom;
   (b) a flap formed of flexible material connected to said top of said swinging door; and
   (c) said flap being of size sufficient to cover said leg receiving opening when said door is closed.

9. A boot and foot warmer as in claim 6 and wherein:
   (a) said door is slanted outwardly from the bottom.

10. A boot and foot warmer as in claim 9 and wherein:
    (a) said side walls include slanted front edges for slanting said door outwardly from the bottom.

* * * * *